(12) United States Patent
Kraus

(10) Patent No.: US 7,873,525 B1
(45) Date of Patent: Jan. 18, 2011

(54) METHOD AND SYSTEM FOR OUTCOME BASED MEDICAL REFERRALS

(76) Inventor: David Ray Kraus, 46 Flagg Rd., Southboro, MA (US) 01772

( * ) Notice: Subject to any disclaimer, the term of this patent is extended or adjusted under 35 U.S.C. 154(b) by 1063 days.

(21) Appl. No.: 11/232,779

(22) Filed: Sep. 22, 2005

Related U.S. Application Data

(66) Substitute for application No. 60/615,165, filed on Oct. 1, 2004.

(51) Int. Cl.
G06Q 10/00 (2006.01)
G06Q 50/00 (2006.01)
(52) U.S. Cl. ......................................................... 705/2
(58) Field of Classification Search ................. 705/2, 705/3, 4, 37; 702/182; 600/300; 514/252.18
See application file for complete search history.

(56) References Cited

U.S. PATENT DOCUMENTS

| | | | | |
|---|---|---|---|---|
| 5,471,382 A | * | 11/1995 | Tallman et al. | 600/300 |
| 5,572,421 A | * | 11/1996 | Altman et al. | 705/3 |
| 6,014,629 A | * | 1/2000 | DeBruin-Ashton | 705/2 |
| 2002/0065758 A1 | * | 5/2002 | Henley | 705/37 |
| 2003/0061006 A1 | * | 3/2003 | Richards et al. | 702/182 |
| 2005/0130986 A1 | * | 6/2005 | Eklund | 514/252.18 |

* cited by examiner

Primary Examiner—Gerald J. O'Connor
Assistant Examiner—John A Pauls
(74) Attorney, Agent, or Firm—Paul E. Lewkowicz; Paul E. Lewkowicz P.C.

(57) ABSTRACT

A method and system is described to provide outcome data to the healthcare industry allowing for fair and accurate quality based purchasing decisions. The system deploys methods to facilitate the accurate and unbiased collection of patient outcome data. From this data warehouse of outcome data, purchasers can access aggregate outcome data identifying those providers or health plans that have achieved the best outcomes for specific criteria. Similarly, individual patient referrals can be made to providers with the best track record of helping comparable patients. Based upon outcome assessment data these searches can automatically be made based on specific patient characteristics and needs.

8 Claims, 13 Drawing Sheets

Overview

FIG. 4

Find a Doctor

To find the best doctors in your area choose an area of specialization (e.g. oncology) or allow the computer to locate a more specific specialist based on your medical issues.

400 {

401 — Choose a specialty     [ Specialization Area ▽ ]

And/Or  NEW!

401a — Choose the best provider based on my assessment results     ☐ Let the computer assist in your selection of the best possible providers based on my symptoms 402 — Enter your zip code     [                    ]

403 — Maximum distance you are willing to travel     [ 5 miles           ▽ ]

404 — Insurance coverage     ☐ Providers must accept my insurance

405 — Choose insurance plan     [ Insurance plan    ▽ ]

406 — More options     ☐ Check this box if you would like to further limit your search (e.g. gender, ethnicity, etc.)

FIG. 5

Find a Doctor Results

*500*

501 { Here are the results of your search.
Click here for help

| NAME | RATING (100 best) NEW! | MILES | INS ACCEPTED | PHONE |
|---|---|---|---|---|
| Dr. A | 95 | 4 | YES | (222) 444-5551 |
| Dr. B | 94 | 1 | NO | (222) 444-1111 |
| Dr. C | 58 | 2 | YES | (222) 444-3333 |
| Dr. D | Not enough info | 1 | YES | (222) 441-4321 |
| Dr. E | Not participating | 2 | YES | (222) 441-1234 |

Find a Doctor Algorithms

Fraud Precautions

FIG. 12a

1201
- The last time you used this site was about how long ago? [Choose one ▽]
- You most frequently use this system at what locations? [Choose one ▽]
- The last time you used this system was about what time of day? [Choose one ▽]

1202
- In what city were you born? [Choose one ▽]
- How old were you when you had your first drink of alcohol? [Choose one ▽]
- How old were you when you first broke a bone and had to wear a cast? [Choose one ▽]

1203
- This is a quick test of your memory. During your last visit to this site we asked you to remember the color of a word. Please choose the right color and type in the word. [Choose one ▽] [          ]

FIG. 12b

Is this the typical computer that you use for WellnessCheck?  Choose one Hope your trip last week went well. Where did you go?  Choose one Whose birthday is coming up next in your family?  Choose one How many brothers does your father have?  Choose one 1204 { Is this rating of your quality of life for this week better or worse than last week?  Choose one What is your boss's first name?  Choose one 1205 { During the next week, what is the event that you are looking forward to the most? Please type a brief description and choose the adjective that best describes your expectations.  Choose one

METHOD AND SYSTEM FOR OUTCOME BASED MEDICAL REFERRALS

CROSS REFERENCE TO RELATED APPLICATIONS

This application claims the benefit of Provisional Patent Application Ser. No. 60/615,165 filed on Oct. 1, 2004 by the present inventor.

BACKGROUND OF THE INVENTION

1. Field of Invention

The present invention relates to the dissemination of healthcare outcome data.

2. Background of Invention

Healthcare expenditures exceeded $1.5 trillion in 2003, as estimated by the Centers for Medicare and Medicaid Services (CMS). This number exceeds 14% of the Gross Domestic Product (GDP), and the country should be able to expect that these enormous healthcare dollars be spent wisely. They are not. Sadly, healthcare purchasing decisions are rarely made based on service quality. This unfortunate reality occurs at every decision making level in the healthcare system. Purchasers of healthcare (e.g. employers, government), make almost all of their decisions based on cost. Payers of healthcare (e.g. insurance plans, HMOs, PPOs) empanel their networks and design prior authorization strategies to contain the cost of care. Consumers of healthcare (patients) typically have some level of choice in their "purchasing" decisions (e.g. deciding what doctor to see), but these decisions are more often based on a referral, recommendation, or convenience. Referrals are often the industry's best approximation for quality purchasing; however, referrals are more often linked to who knows whom, and an individual's prestige, rather than accurate and unbiased measures of quality. At all of these levels, the primary reason for this glaring problem in the healthcare industry is a lack of access to reliable and trusted quality data that can be easily obtained on-demand.

Reimbursable providers of healthcare (e.g. hospitals, doctors, licensed social workers, physical therapists, nurses) do have ethical and legal obligations to improve the quality of life for their patients and typically fight hard for what they believe is best for their patients. However, they are not often reimbursed for delivering good quality and their treatment decisions are more often based on how they were trained rather than what has been proven to work since they left graduate school. Federal agencies mandated to help discover and promote good healthcare (e.g. the National Institute of Health [NIH], and the Agency for Healthcare Research and Quality [AHRQ]) have current and long standing programs to help solve this "dissemination" problem—helping professionals stay current with what has proven to work best. These long-standing programs have made little inroads into the source of the problem, and it still can take 10-20 years for advances in treatment to work their way down into the mainstream. Unfortunately, it has not been a priority for healthcare providers of all types to stay current with what research has proven to work best (staying current). The few providers that do stay current are not commensurately rewarded by increased business because their success is not measured, benchmarked, or made publicly available. There is strong data and common sense to support the notion that if such data was made easily accessible to purchasers "just in time" that there would be a dramatic shift in both the quality and overall cost of healthcare. Quality would improve by natural market forces; and by eliminating ineffective and inefficient services, overall expenditures would decrease.

Most patients have some degree of choice in the selection of their healthcare providers. Some patients have complete and open access to be treated by the provider of their choice, while most have their choices limited by "quality" and cost containment strategies like network membership and authorization requirements. Nevertheless, even in the most restrictive managed care plans, patients still have choices. However, these "choices" are rarely exercised based on outcome data that can clearly identify providers that have the best chance of helping their current conditions. In most cases this data is not available to them.

The Internet is a logical platform for such data to be made accessible. In fact, the US population searches the Internet for health related content more than any other topic. Conventional "find a doctor" (FAD) services on the Internet deliver provider listings based on geographic location, typically one city at a time (e.g. the American Medical Association's FAD). To be included on such a list, providers usually must be licensed and credentialed. For most listings, these FAD services are essentially an electronic yellow page listing. For these FADs there are no current mechanisms available to sort or search based on quality.

FIG. 1 provides an overview of the prior art. In these conventional FAD services a simple database of listed providers (103) is made accessible in an output format (104) to users through simple queries (102), filtering the contents of the list by basic data like zip code. A few services add to this process some basic, unscientific patient feedback (101) like consumer satisfaction.

The few services that do deliver access to satisfaction data do so without any scientific methodology that ensures data accuracy and such services list strong disclaimers that the data is not scientifically accurate. In most cases the mode number of responders to satisfaction data is zero to two patients. The data is further biased by the self-selecting nature of the process. Only patients that make a point of returning to the website and completing a satisfaction questionnaire are included in the publicly available results. Obviously these motivated consumers are a biased sample and rarely reflect the overall quality of the provider. Furthermore, there are no safeguards that ensure that the provider and/or their staff completed these surveys and there is no ability to sort or select based on these crude outcome statistics. In essence, the feedback solicited and disseminated in these services mirror the feedback on other websites including on-line bookstores and auction houses. Rather than being an afterthought these data should be the heart of FAD services and should be designed appropriately. The present invention addresses these concerns allowing access to high quality provider ratings. In other words, FAD services must be linked to outcomes databases that are routinely providing high quality assessment and diagnostic tools to providers, as part of routine and standard care.

Another limitation in the prior art is the lack of risk-adjustment methodologies to adjust outcome data to control for the level of difficulty of each patient's problems. Some problems are easier to treat, and even with the same problem, some patients have other issues that make treating that problem more challenging. For example, treating a broken leg is more challenging if the patient is also a paraplegic and has no feeling in his extremities. Fair provider comparisons must take these variables into account and statistically risk-adjust the data accordingly.

Another significant limitation of the prior art (even when provider ratings are made available) is the often-misleading feedback that comes from overall summary scores. When a consumer is looking for a specialist to treat a specific problem, it is probably most important to receive feedback on cases with similar problems as measured by outcome tools that are tailored to the specific conditions. Overall satisfaction ratings and summary scores may provide useful supplementary information, but if a parent is trying to find the best specialist to treat her child who has life-threatening asthma and allergies, the primary concern should be what the various providers have done with similar cases in to reduce breathing problems and other related issues, not patient satisfaction or general patient quality of life. Many healthcare providers supplement their income by providing multiple services. In the asthma example above, it is quite possible that many of the specialists that could treat the child also serve as pediatricians or primary care physicians. These physicians will have patients that are being treated for routine exams, sore throats, and many other mild and transient conditions. Overall patient satisfaction ratings or general improvement of quality of life across all of these patients may be interesting and useful information to assess. However, it probably is not detailed or specific enough to help a parent or consumer make a purchasing decision. For most consumers in this situation it will be more useful to rank providers based on the measure that is most related to the specific problem (e.g. breathing). Similarly, for an HMO or PPO looking to improve their network in a specialty area, these overall ratings are fairly useless in helping to empanel the best-qualified provider for the needs of the network. Again problem specific measures (also referred to as "domain" measures by those of ordinary skill in the art) are most relevant.

In summary, electronic FAD services have great potential in helping to transform the healthcare industry that makes decisions based on quality and efficiency. However, there are significant improvements that are needed in order to fulfill this promise. Most importantly, the current art is not linked to clinically useful and accurate outcome databases, does not allow user filters or input for clinical needs and risk-adjustment variables, and does not employ the necessary algorithms to facilitate purchasing decisions based on quality.

SUMMARY OF INVENTION

In accordance with the present invention we define a powerful system and method to collect and disseminate accurate healthcare outcome data. By answering questions about their current health status, the invention assists patients in identifying professionals that have achieved the best outcomes with other patients with similar conditions and problems (i.e., in the same domain). These recommendations are provided by taking the results of health status questions, linking them to a large and growing database of healthcare outcomes, and using defined algorithms to locate the best providers. By using the search and filter algorithms, others within the healthcare chain can gain access to lists of providers, hospitals, HMOs, etc. that have achieved the best outcomes in select domains.

BRIEF DESCRIPTION OF DRAWINGS

The accompanying drawings, which are incorporated in and constitute a part of the specification, illustrate an exemplary embodiment of the present invention.

FIG. 4 is a screen shot of how one embodiment of the present invention assists a patient in finding a doctor who specializes in an area of interest and who possesses the best outcomes in treating conditions in this specialization area;

FIG. 5 is an example of how one embodiment of the present invention can present the summary results of a "find a doctor" search;

FIG. 12A provides examples of the types of questions used by one embodiment of the system to assess for fraudulent activity;

FIG. 12B provides additional examples of the types of questions used by one embodiment of the system to assess for fraudulent activity.

DETAILED DESCRIPTION

Figure 1:
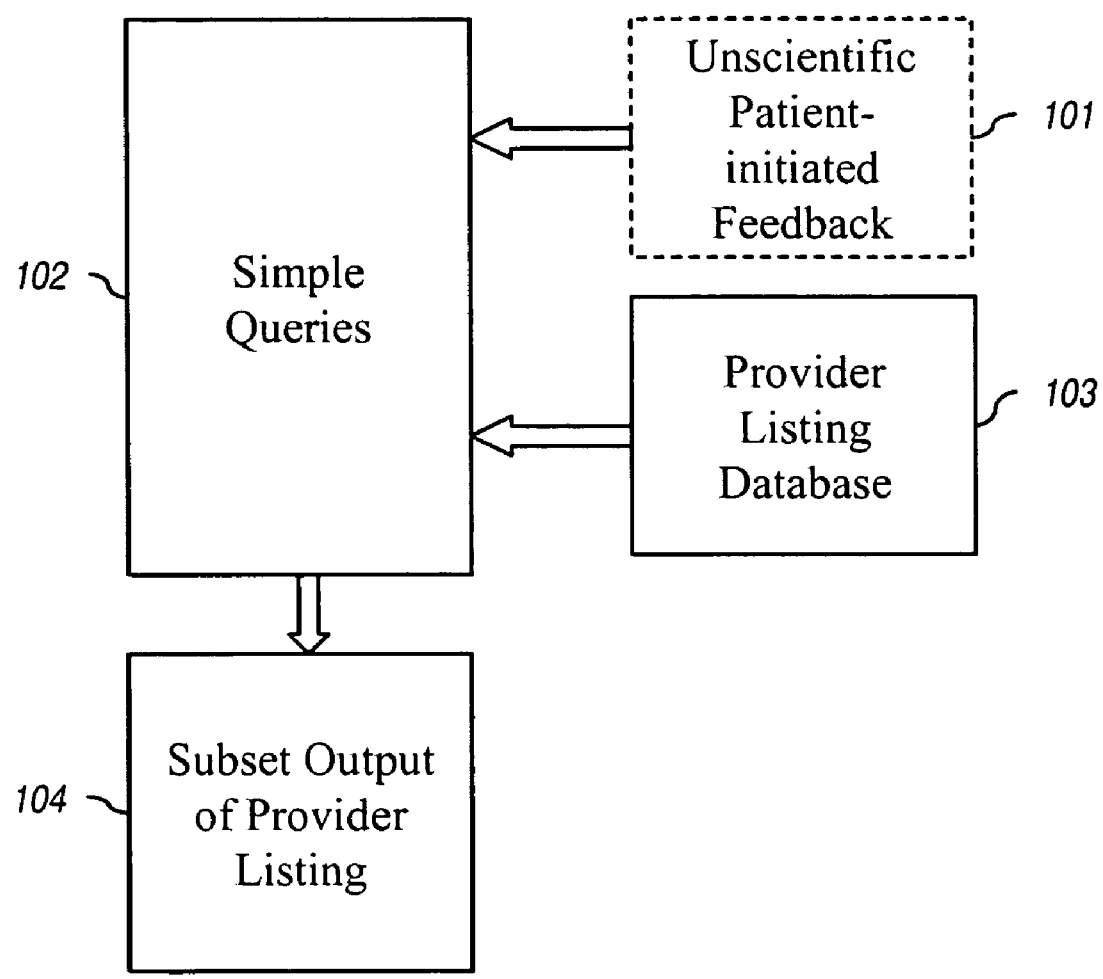
FIG. 1 is an overview of the prior art.
Figure 2:
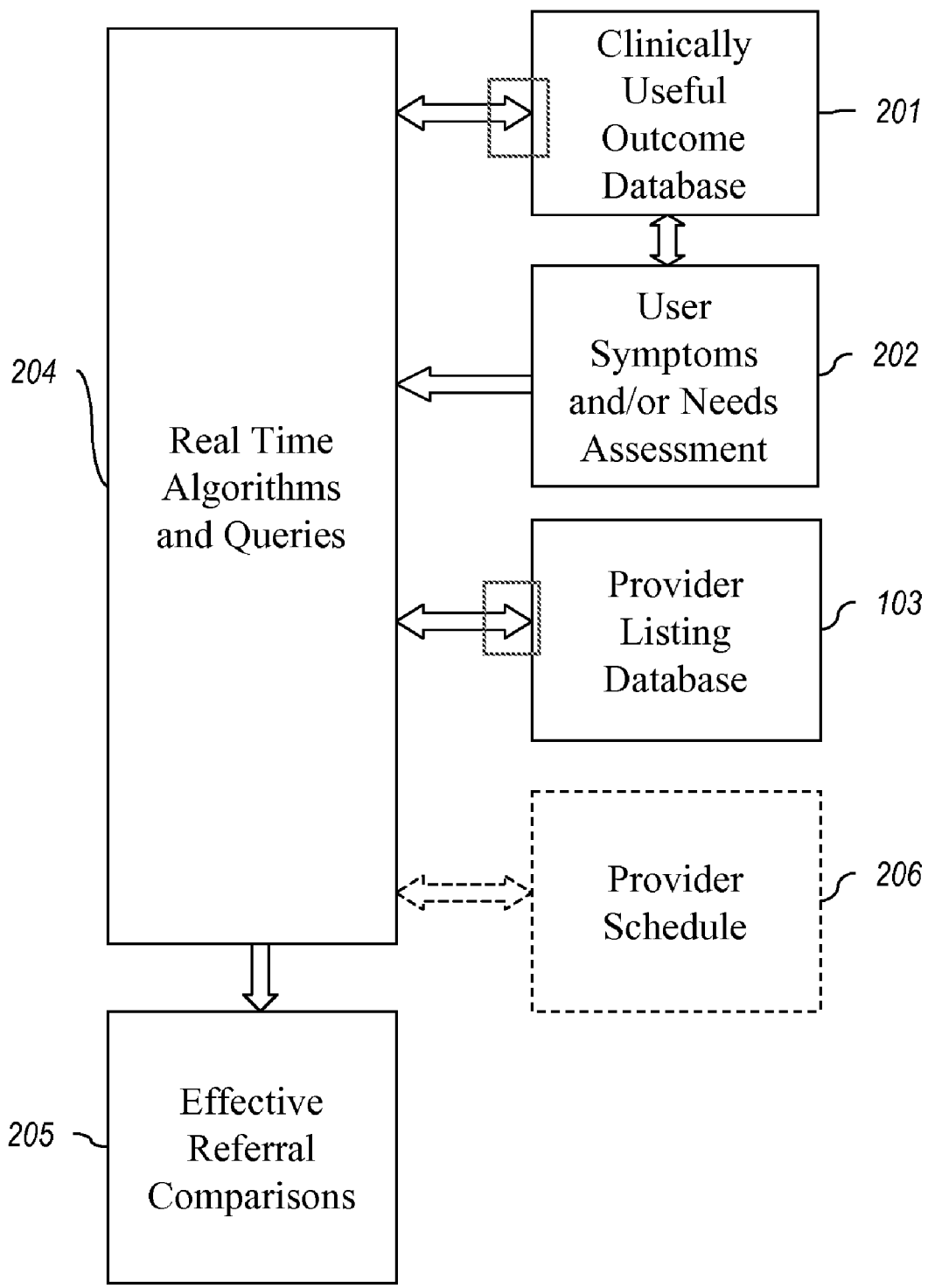
FIG. 2 is an overview of an exemplary embodiment of the current invention.

FIG. 2 is an overview of an exemplary embodiment of the current invention that facilitates dissemination of medical outcome data. The system improves upon the prior art by linking searchers and queries to an ongoing and clinically useful outcomes management database (201). As will be discussed in detail below, database 201 is actively used by patients and providers in the clinical management of patient care. Doing so ensures that the outcomes database is filled with the types of data that actually help to predict and measure client improvement in the current healthcare environment and is updated and modified to meet these expanding needs. Integrated in this way the data is likely to be the most useful data in ranking providers and making referrals. It also ensures that database 201 is filled with the most accurate data as it is used as an essential part of patient assessment and care.

The system is further enhanced by a full assessment of the user's symptoms and/or needs (202) that includes both logistical needs (e.g. geographic and insurance limitations) and clinical needs (e.g. chief complaints, problem severity, and diagnostic data). Through these inputs, real-time queries and algorithms (204) generate the most effective referral comparisons (205) that are tailored to the patient's needs and provider ratings based on the unique characteristics that matter most to each individual patient. It is envisioned that providers, managed care companies, and patients themselves will be able to access this system to make the most accurate referrals possible. Rather than relying on word of mouth and conjecture, referrals can be made based on a customized analysis of clinical outcomes. In another embodiment of the present invention, this data can be augmented by access to the provider's schedule to check availability of appointments and schedule the referral on-line (206).

Figure 3:
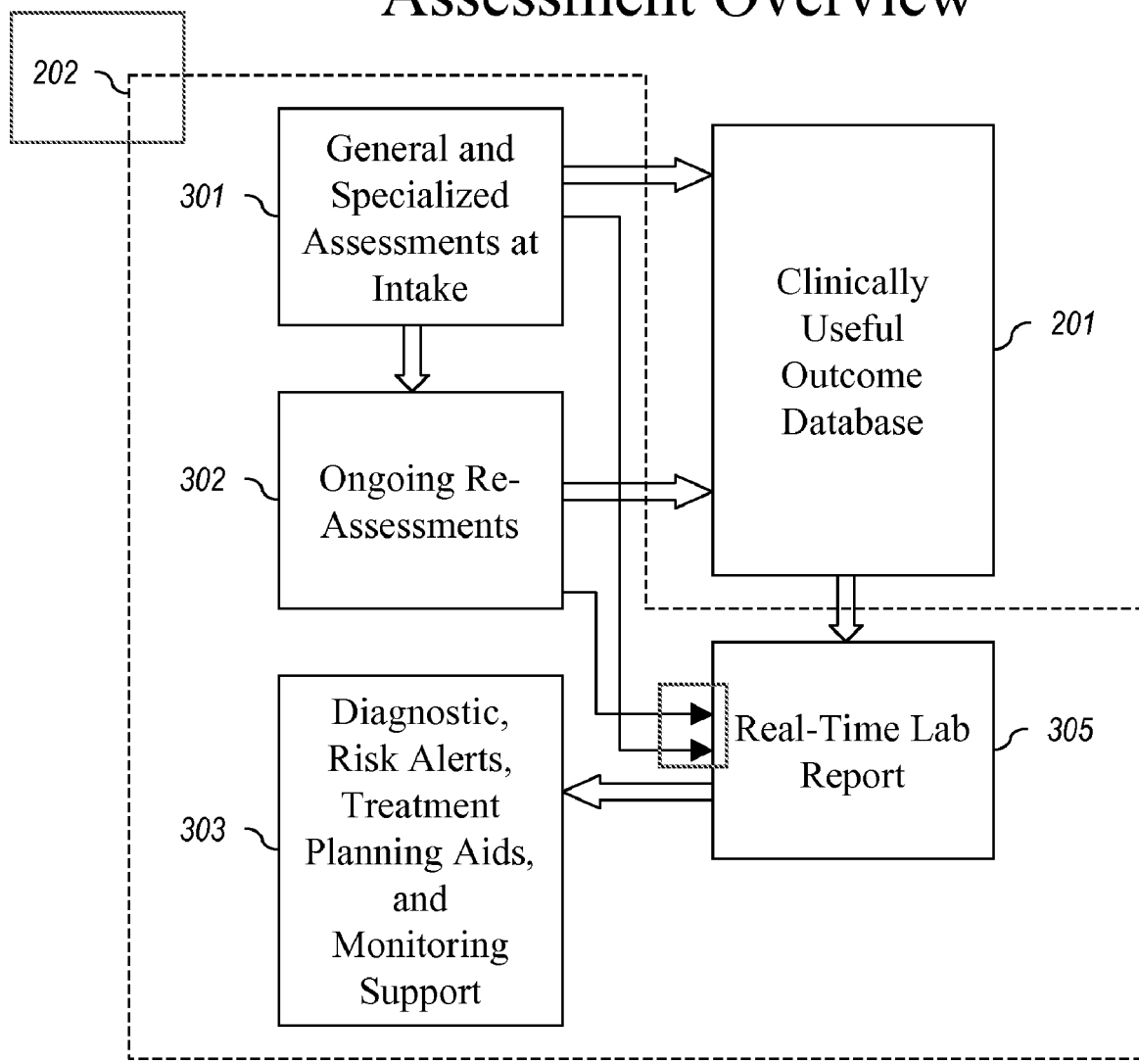
FIG. 3 is an overview of the assessment process in the preferred embodiment of the present invention.

FIG. 3 is an overview of the assessment process 202 in the preferred embodiment of the present invention. In this preferred embodiment the clinically useful outcomes database (201) is continually updated by constant provider use in the assessment, tracking and monitoring of all patients through all phases of the treatment process including post-discharge. As a patient starts treatment, general and specialized assessments are administered (301) and the results stored in the database (201). In the preferred embodiment, these assessments will include both general measures of health status, general well being, and quality of life, as well as specific measures of disease symptoms and recovery for each major medical problem. Branching algorithms and business logic can quickly guide the patient to the specific tools for their condition (e.g. the inventor's previous patent application Ser. No. 10/689,270).

These assessments trigger real-time lab reports (305) that are used by the provider for multiple purposes (303) including but not limited to diagnostic decision support, risk alerts, treatment planning, and treatment progress. Similarly, ongoing re-assessments (302) also populate the database (201) and generate real-time reports (305) that are used to track progress and modify treatment plans.

Other embodiments of the present invention do not require that the outcome data be used by the provider in this format. However, it is believed that this preferred embodiment ensures that the assessment and outcome data follow the market and provider needs and will have the best chance of deciphering the most trusted referrals. For example, another embodiment could randomly collect outcome data from a subset of patients and not generate provider reports. Another embodiment may generate reports for the patient, provider, and/or payer.

FIG. 4 is a screen shot of how one embodiment of the present invention assists a patient in finding a doctor who specializes in the area of identified need and who possesses the best outcomes in treating this type of condition. Through user input and preferences (400), the process identifies the most appropriate providers. In this embodiment, the patient can select an area of specialization (domain) directly (401), and/or allow (401a) an auto-defined query (ADQ) to assist in determining the most appropriate sub-specialization based on the assessment tool (FIG. 3). Access to quality outcome data through either technique is unique and innovative; however, the ADQs allow for more focused and tailored referrals. For example, specialization dropdown list options (in 401) might include various specializations in medicine and related healthcare fields (e.g. primary care, OB-GYN, Oncology, Psychiatry, Physical Therapy, etc.). Other embodiments of the present invention could also provide sub-choices. For example, within psychiatry sub-choices might include Depression, Substance Abuse, Anxiety, Psychosis, and Bipolar. However, with ADQs, the sub-selections can become far more focused and precise. Continuing the psychiatry example, most patients with psychiatric problems are not aware that their problems are psychological in nature. Instead they focus on issues like fatigue, sleep problems, stomach aches, and blood pressure issues—all of which could be symptoms of psychological rather than medical problems. A patient with Mild Dysthimia might not even know that his problem is related to a form of depression and has no clue what Specialization Area to select. Even if he were aware that the issue is related to depression, he probably would not know that the issue is Dysthimia rather than Major Depression unless he had received previous treatment for the condition, and certainly would not be qualified to know that the condition is currently in a mild form rather than moderate or severe. However, the assessment tool results would have diagnosed the condition and could be used to search the database for a list of providers who have an excellent record of treating patients with mild Dysthimia—a far better matching system than anything currently available.

In summary, the ADQ feature offers powerful advantages in providing more refined searching and eliminating the need of the consumer or user to precisely classify and define the problem, or to determine which subspecialty is most appropriate.

In this embodiment of the present invention users can further limit their searches by entering their zip code (402), maximum distance willing to travel (403), insurance company (405), and whether this insurance must be accepted (404). Other embodiments of the present invention can provide other options to help limit, sort, and filter providers. These options can be made available on the primary screen (FIG. 4) or the less commonly used options can be accessed with the more option button (406).

For example, some patients may feel other factors in their lives require more focused queries. In the preferred embodiment of the present inventions, any demographic or clinical variable measured (FIG. 3, 301) is available for user filtering. These additional selections could include gender, racial, or religious variables where patients from minority groups might want to ensure that the doctor has been sensitive to cultural issues that can interact with health status and patient recovery. In addition, other clinical variables can be important in certain situations and could be made available here. For example, in the treatment of heart disease with co-morbid depression or anxiety disorders, relapse and recovery can be challenged and it may be important to focus searches based on these additional clinical variables. An informed consumer will want evidence that the prospective providers have experience dealing with these important issues.

The more focused the search, the greater the chance that results will produce limited options (e.g. few providers with track records treating the exact same problems and conditions). However, the present invention allows patients to focus their searches on the areas of importance to them and relax the restrictiveness of their searches until they are satisfied. Again, any variable collected through the conventional assessment/outcome questionnaires can be used to sort and limit FAD searches in the preferred embodiment.

FIG. 5 is an example of how one embodiment of the present invention can present the summary results (500) of a FAD search. Each provider is identified by name (502) and initially sorted by their relative ranking (503). In this embodiment ratings are normalized with 50 representing an average score and 100 the maximum score. As will be discussed in detail below, these rankings are tailored to the issues that are most important to the user, and unless requested, do not represent an overall ranking across all patients with general outcome results. Instead, they represent the relative outcome ranking for the subset of patients who have the specific types of problems of interest as measured by the most appropriate outcome variables for that disorder. If there is not enough reliable information to provide a rating for a specific provider their ranking is marked with "not enough info" (508). In addition, if a provider refuses to participate in the outcome monitoring feature of the referral system, these providers will be listed as "not participating" (509). Market forces will likely sway most of the late adopters to join if the product is found to be useful and referrals begin moving to those providers that are participating.

The results also provide the relative ranking score (503) that provides information on relative difference in quality between one provider and another. In this example, the highest possible score is 100 and both Dr. A and Dr. B have rankings close to this ideal. However, Dr. C is a distant third in the rankings, yet still above average. This type of relative ranking can be invaluable information in making informed treatment decisions, especially in rural areas where there may be few medical options. In addition, this summary table provides relevant distance information (504), insurance coverage information (505), and basic contact information (506). If the user clicks on the doctor's name (e.g. 507), detailed doctor specific practice information would be highlighted. This information typically includes a paragraph written by the doctor detailing his/her areas of interest, license and training information, insurance accepted, office locations, and contact information.

By clicking the help function (501), users can receive detailed instructions on how to sort the summary information based on other criteria (e.g. distance to travel or average wait times to get an appointment), how to print the list, or automatically send the doctors an email of their assessment tool results with an inquiry about their availability to take on a new patient.

Figure 6:
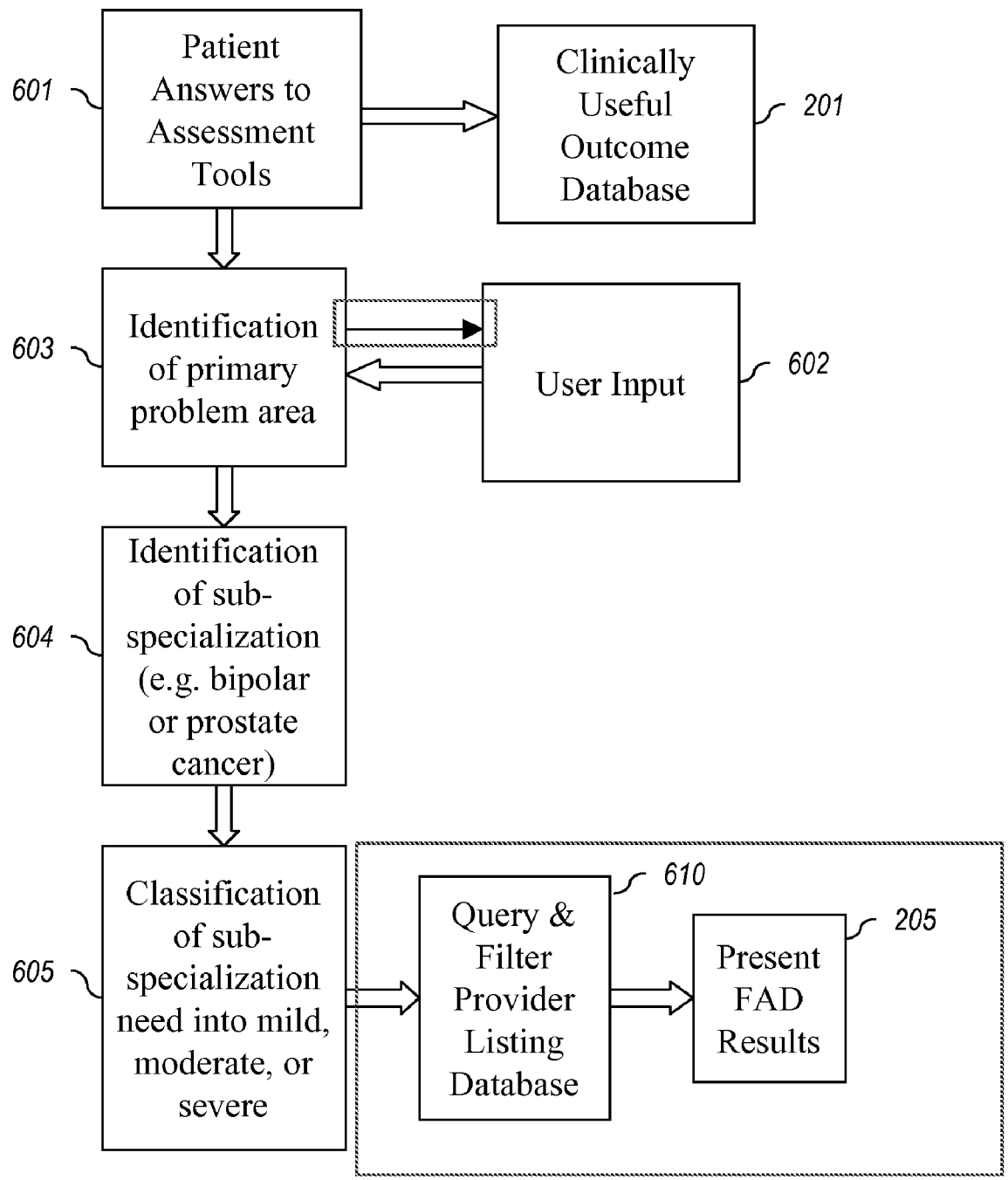
FIG. 6 is a flowchart of how one embodiment of the present invention creates an auto-defined query.

FIG. 6 is a flowchart of how one embodiment of the present invention creates an auto-defined query that is executed if the user chooses option 401*a* in FIG. 4. Patient answers to assessment tools (601) are permanently stored in the outcome database (201). Based on assessment tool results the primary problem areas (or domains of interest) are identified (603) through an algorithm that takes into account the seriousness of the problem (e.g. Is it life threatening?), and how abnormal the problem is (i.e. identifying the problem that is the most out of the norm. For clarity, this most-out-of-norm problem is referred to herein as an "abnormal domain of interest.") If more than one area is identified, the user is prompted to select the area to be used as the primary search criteria (602). Based upon the specifics of the questionnaire results a primary sub-specialization is chosen (604). For example, if an orthopedic surgeon is needed and the problem is with the left thumb, hand surgeons are automatically selected as the sub-specialty. Finally, the severity of the patient's problem is classified in currently known medical severity (e.g. Stage II cancer) or if no standard classification exists, using mild, moderate, and severe (605). This information is then used to query and filter the database and represents a significant improvement over the prior art. In fact, such a query may be more accurate than the current "state-of-the-art" in medical referrals—a personal recommendation. A personal recommendation from another patient or a physician is usually based upon one or two personal experiences. Most healthcare providers have no detailed knowledge of their own relative strengths and weaknesses, let alone the relative strengths of other providers. The ADQs provide the best source of information on the most effective providers for the identified problems and could dramatically improve the quality of care to millions of patients.

Figure 7:
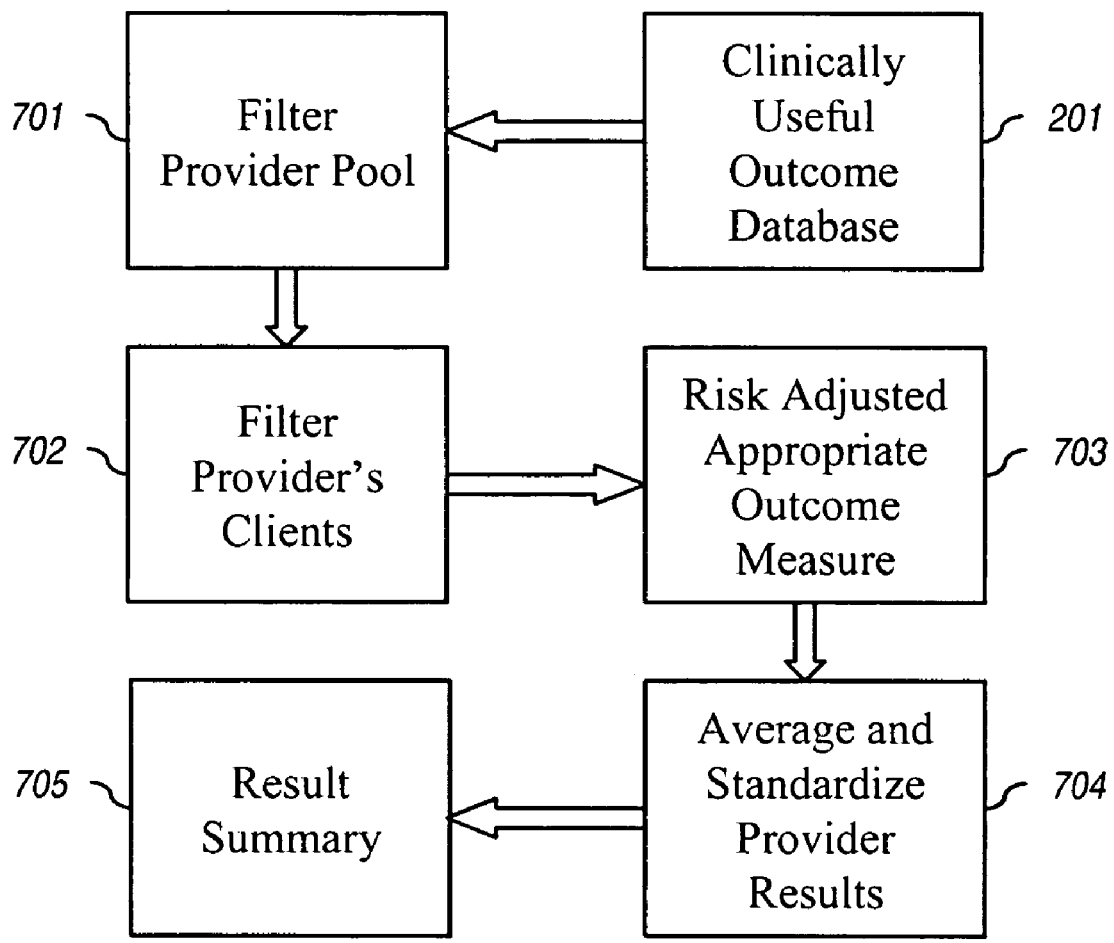
FIG. 7 is a flowchart of the basic steps taken in the present invention to deliver find a doctor results.

FIG. 7 is a flowchart of the steps taken in the present invention to deliver find a doctor results. In preparation for these procedures, the outcome data (201) stored in the data warehouse (i.e., the time-based outcomes database) is filtered by user- or auto-defined queries, limiting the potential provider listings (701) based on various criteria already identified, including geography, specialty, and insurance needs. Next the remaining provider's patients are filtered (702) for conditions and problems that match the current user's needs (e.g. FIG. 6). The resulting outcome dataset is then risk-adjusted (703), averaged and standardized (704) for each provider, yielding the results summary (705). In the preferred embodiment these calculations are done in real-time to ensure the most accurate and up-to-date results.

Figure 8:
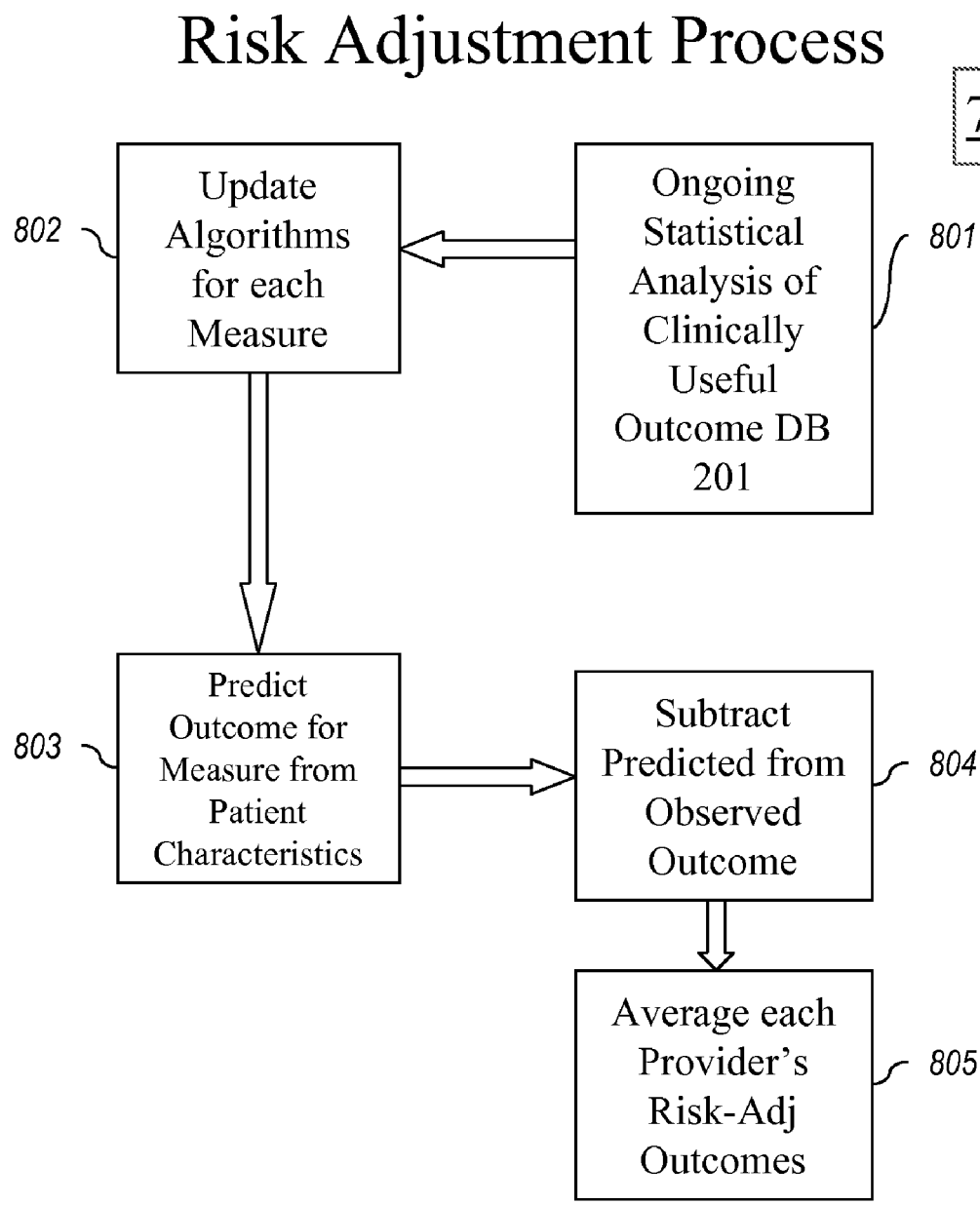
FIG. 8 illustrates how one embodiment of the present invention integrates risk-adjustment procedures.

FIG. 8 illustrates how one embodiment of the present invention integrates risk-adjustment procedures 703 (from FIG. 7) to ensure that the provider comparisons are fair and accurate. Risk-adjustment techniques statistically adjust each patient's outcome results for the relative severity of the case and any factors that can make the case more difficult to treat. For example a cancer patient with AIDS is typically more difficult to treat than a patient who is not HIV positive. Although raw outcome results can be used to compare providers, more accurate results are achieved by risk-adjusting the data. Risk-adjustment variables include any variable that can affect the outcome of treatment that is outside the control of the provider. In many cases, this includes variables like the initial severity of the problem, the presence of co-morbid medical problems, the amount of social or financial supports, and many others.

In this embodiment, the risk-adjustment algorithms 703 are continually re-assessed with standard statistical techniques (in step 801), with algorithms updated for each outcome measure as necessary in step 802. These algorithms are then used to predict the amount of change that should be expected for each patient in step 803. This risk-adjusted predicted score represents the average amount of improvement that the average provider obtains with similar patients. When a provider gets better results than this predicted average it represents better than average outcomes; whereas, if they get poorer results, it represents worse than average outcomes. This is measured by subtracting the predicted score from the outcome actually observed for each patient (804). These subtracted scores are then averaged for each provider (805) and provide the basis for the fairest comparisons of provider quality.

Figure 9:
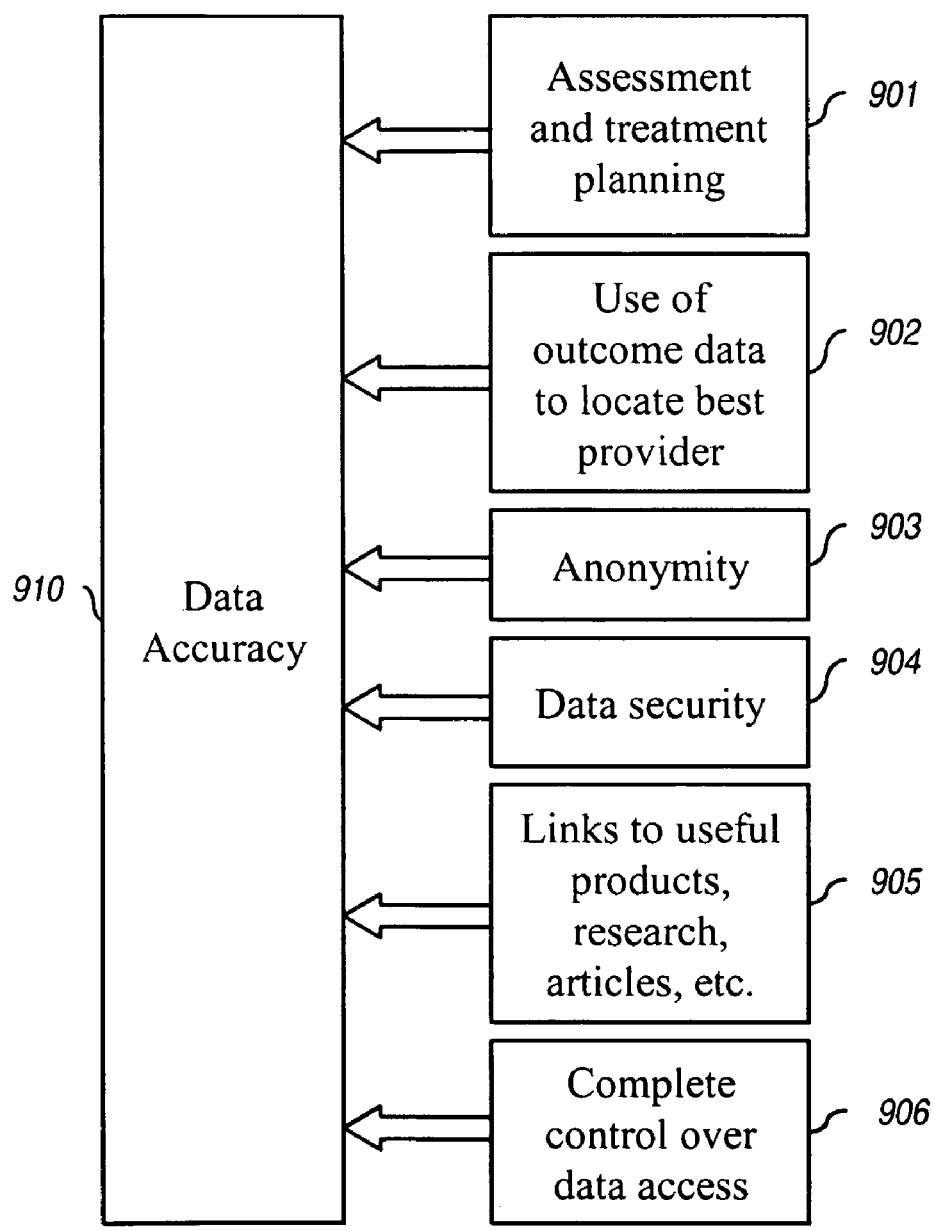
FIG. 9 illustrates how one embodiment of the present invention integrates features to ensure the accuracy of the data stored in the outcome database.

FIG. 9 illustrates how one embodiment of the present invention integrates features to ensure the accuracy of the data stored in the outcome database 201 and used to generate the most accurate referrals. Obviously, data accuracy is essential if the provider comparisons and resulting referrals are going to be useful. Unlike conventional outcome data collection systems, an embodiment of the present invention integrates unique features that maximize the accuracy of the data collected. Without such features those answering assessment questions should worry about how the data will be used and may not be comfortable answering questions honestly. For example, if an employer received access to the information, most people would likely alter their answers to questions fearing how the employer would use the information. Similarly, if a provider is answering assessment questions about their patient's health status and fears that the data could be used without their patient's informed consent, they will be reluctant to participate in the data collection process.

Data accuracy (910) is maximized by integrating Hippocratic principles that have served medicine well for centuries. Based on the Hippocratic oath—"do no harm," medical professionals are bound to only do things that facilitate the welfare of their patients. Patients in return understand that the only way a professional can help them is to provide the most accurate information. These principles have led to the legal rights of confidentiality, medical ethics, and doctor-patient privilege. In the preferred embodiment of the present invention, data is protected and used so as to maximize these Hippocratic principles. First, the data collected is used to assist in screening, assessing, diagnosing, treatment planning, and treatment plan monitoring (901), as discussed previously (e.g., via element 202 of FIG. 2). This ensures that both the patient and provider place the proper emphasis and importance on the need for accuracy in order to maximize the effectiveness of care. Similarly, the data (in the form of patient needs assessments [FIG. 2, 202]) is used to help locate the best provider (902) via process 700 of FIG. 7. Accurate responses to these questions help to locate the provider that has the best track record of treating similar problems. In addition, patient data can be used to help patients locate other resources and information beyond medical referrals (905). This can include self-help groups, books, research articles, medical products, and other links that have been proven to help patients with similar problems.

Furthermore, it is vital to ensure that the patient has complete control over their personal and private data (906). Each patient should control whom and at what times, medical professionals can have access to their responses. This permission should easily be granted and withdrawn at any time. There should be no personally identifiable information in the system making each patient anonymous (903). As such, each patient can set up an anonymous account in the system with nothing that links the data back to an identified person. This includes the lack of email addresses, phone numbers, addresses, social security numbers or any other identifiable data. The data is an island unto itself that can only be accessed by the user with a user name and password that they create (e.g. the inventor's Provisional Patent Application Ser. No. 60/615,376).

Figure 10:
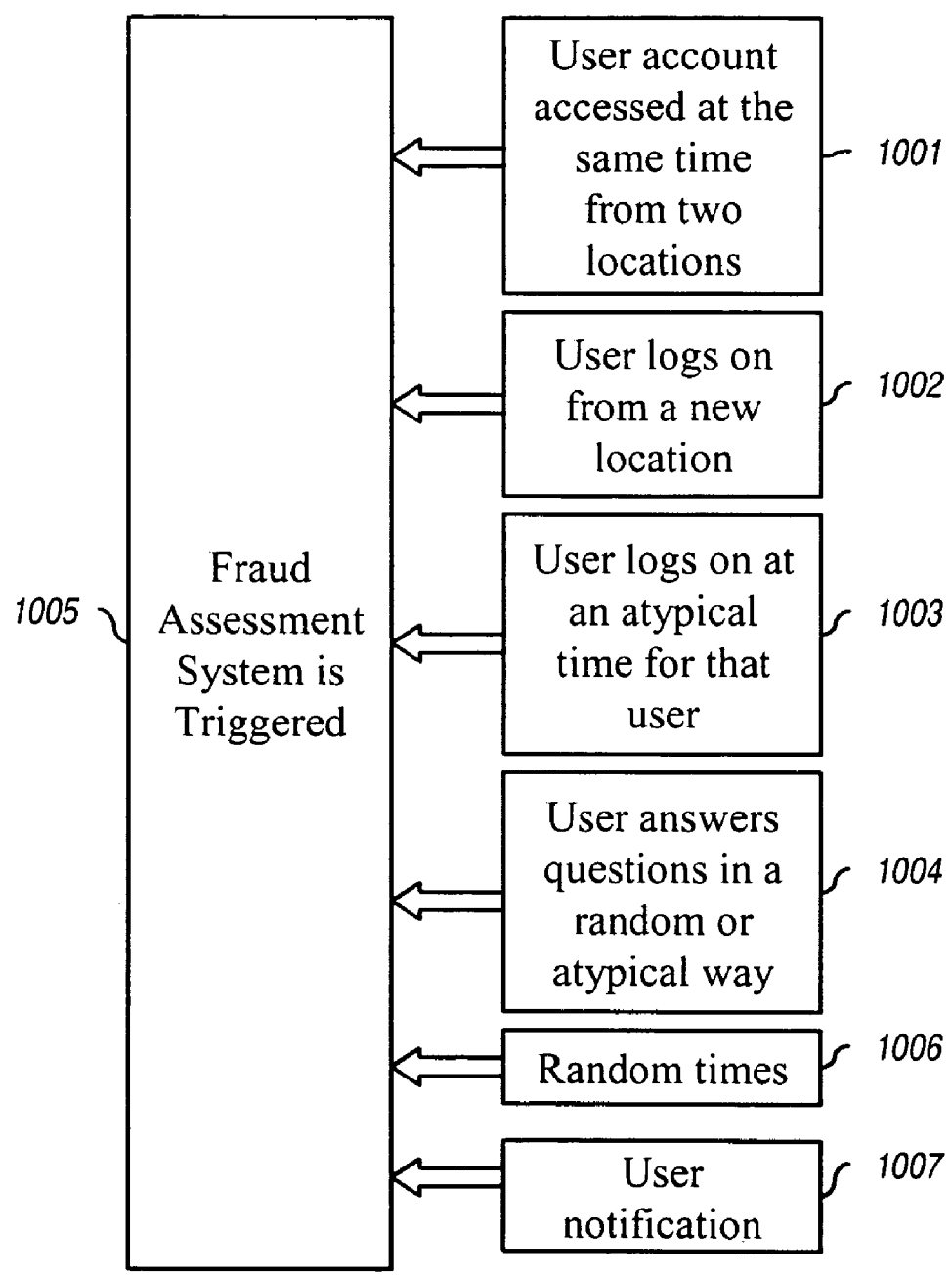
FIG. 10 illustrates how one embodiment of the present invention polices user activity to protect against fraudulent use and ensures data accuracy.
Figure 11:
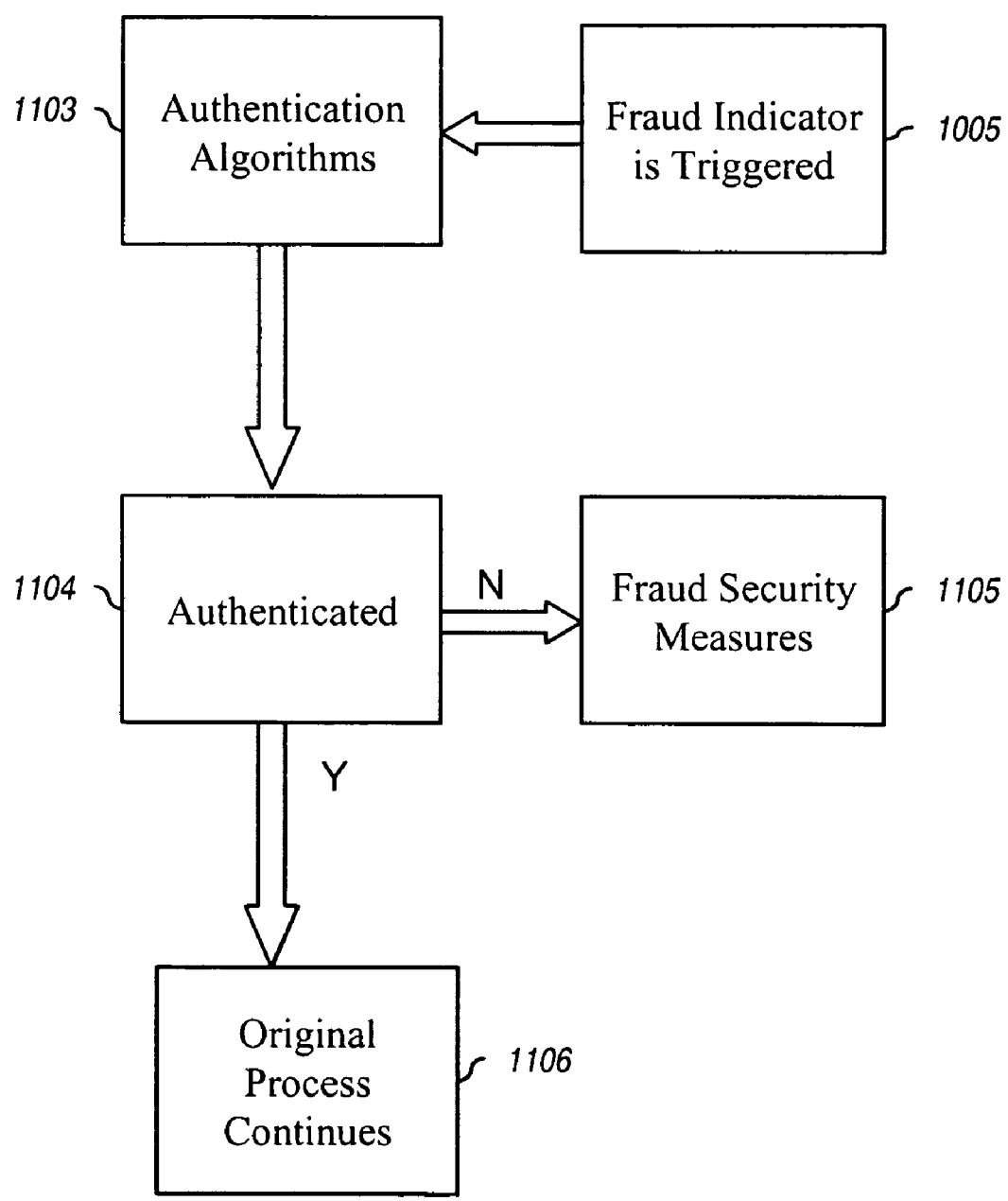
FIG. 11 provides an overview of the fraud precaution process.

Finally, data accuracy is increased with data security protections (904) that are further detailed in FIGS. 10-12. Various embodiments of the present invention can use any, all, or none of these data accuracy protections, however the preferred embodiment uses them all in order to maximize the accuracy of the database.

FIG. 10 illustrates how one embodiment of the present invention polices user activity to protect against fraudulent use and ensures data accuracy. Protections should be in place to prevent unauthorized use of a patient's account. Threats of fraud come from two major sources. The first comes from hackers trying to break in and alter existing datasets, primarily to prove that they can. The second threat comes from those with a vested interest in the outcomes and want to make sure that their data looks as favorable as possible. Unlike conventional outcome data collection systems, the present invention integrates (within user symptoms and/or needs assessment element 202 of FIG. 2) unique features that maximize the chances that no one can fraudulently access a user's account and enter data on behalf of patients or providers. A fraud assessment system (1005) is triggered under certain conditions including: a user account being accessed from more than one location simultaneously (1001); when a user logs on from a new location (1002); if a user logs on at an atypical time for that user (1003); if the user answers questions in an atypical, random, or rapid manner (1004). The system can also trigger fraud assessments on a random basis without an identified triggering event (1006). After users log on, they would be presented with information about the last time they logged on (including location, date, time, duration, and services accessed) so that they can monitor potential fraudulent use and notify the system of a potential security breach (1007).

FIG. 11 provides an overview of the fraud precaution process. After a fraud indication is triggered (1005), authentication algorithms are initiated (1103) to determine if fraudulent use has actually occurred. These authentication measures can include immediate questioning of the user currently on-line, or analysis of historical transaction patterns. If no fraud is indicated and the user is authenticated (1104) then the original transactions or process that was occurring before the trigger (1005) is continued (1106). However, if the user is not authenticated or fraud is suspected, fraud security measures (1105) are enacted which can include shutting down the user's account while a more thorough investigation is conducted. The security measures could also include sending a warning email to the user, eliminate the user's data from the data warehouse or any other action that is deemed appropriate.

FIG. 12 (*a* and *b*) provides examples of the types of questions used by the preferred embodiment of the system to assess for (or trigger on) fraudulent activity 1005. If fraud is very likely (i.e. the user's account was accessed from two locations at the same time) before the user is presented with information about the last time they accessed the system, they can be asked questions (1201) with multiple choice answers about their last system activity. During a user's first assessment about their general medical condition they can be asked some basic questions (1202) that could be asked again in the future if fraud was suspected. The fraud assessment can also be integrated with other standard tests that are required (e.g. tests of memory) as exemplified in (1203). Users can also be asked questions related to the historical and trend information they have been completing over time (1204). In addition, users can be asked about upcoming events that might impact on their health and well being (1205). Such questions can serve multiple purposes, including helping the user feel that the computerized system is acting much like a friend and is interested in tracking important life events, and passes this important information onto providers if authorized. It can also be used to identify unique patient stressors that trigger exacerbations in medical conditions, and assess for fraud by asking follow-up questions at some point in the future.

Other embodiments of the present invention can be created to assist other healthcare purchasers (e.g. employers and governments) in accessing good quality outcome data. For example, an employer or MCO may be the user (in FIG. 2, 202) rather than an individual patient. Their goal of interfacing with the invention may be to find the right group of providers that can fill a certain healthcare need. A large healthcare purchaser may wish to receive outcome data on various healthcare payers and managed care organizations in order to comparison shop. A managed care organization may want outcome data on providers to assist in network development. In each of these embodiments, minor adjustments are made to the front-end FAD questions exemplified in FIG. 4. The system can meet the needs of the customer and still comply with the functionality and methods of this invention.

In summary, the present invention solves two very important and related problems in the healthcare field. First, it provides the industry with the first system and method that delivers outcome-based referrals at the point of service that will have an immense impact on re-organizing healthcare purchasing decisions. Secondly, the invention answers some critical problems the healthcare industry faces in accurately collecting outcome data and preventing fraud. The present invention provides many improvements and advantages over the prior art. It provides scientifically valid outcome data with methodologies and tools that provide accurate comparisons, including state-of-the-art risk-adjustment procedures. The system and method ensures that the data is accurate and imposes safeguards that protect the authenticity and accuracy of the data. Finally, the system and method includes multiple measures of clinical outcome that allow for the selection of the proper measure of comparison to tailor the feedback to each user/patient's needs and concerns.

I claim:

1. A method of patient referral, comprising:
   for each of a plurality of patients each treated by a respective provider, administering questionnaires to each said patient over time, wherein each time a questionnaire is administered, a time-based outcome for each said patient and said respective provider is produced; and wherein each time-based outcome comprises a measure of said patient's change in a medical condition over time; and wherein each time-based outcome further comprises a measure of said respective provider's level of success in treating said medical condition;

storing said plurality of time-based outcomes in a computer-implemented database correlated by at least said respective provider; and on a programmed computer, automatically:

determining the medical condition for at least one of said plurality of patients based at least on said time-based outcome produced by the questionnaire most recently administered to said one of said plurality of patients;

determining the medical specialty of a provider to treat the determined medical condition based at least on said time-based outcome produced by the questionnaire most recently administered to said one of said plurality of patients;

querying said computer-implemented database for specific providers having said medical specialty and having a plurality of said time-based outcomes for said medical condition, said querying resulting in a summary table of said specific providers;

ranking each of said specific providers in said summary table based on each of said specific providers' plurality of time-based outcomes for said medical condition to form a ranked summary table of specific providers, wherein each of said specific providers' ranking is based on the average of the plurality of said measures of said respective provider's level of success in treating said medical condition; and presenting said ranked summary table of specific providers to the at least one of said plurality of patients.

2. The method of claim 1, wherein said questionnaires comprise general health and functioning and disease-specific questions.

3. The method of claim 1, wherein said computer-implemented database is linked to a schedule of at least one of said specific providers to facilitate scheduling of said referral.

4. The method of claim 1, wherein, prior to said automatically determining, the plurality of time-based outcomes for said plurality of patients is risk adjusted.

5. The method of claim 1, wherein said automatically determining further comprises identifying at least one abnormal medical condition, wherein said abnormal medical condition is the specific medical condition for each patient that is the most out of the norm.

6. The method of claim 5, wherein said automatically determining further comprises using a weighting of a severity of said at least one abnormal medical condition.

7. The method of claim 1, wherein said querying further comprises filtering on non-outcome-based criteria.

8. The method of claim 7, wherein said non-outcome-based criteria are selected from a list consisting of distance to travel, gender, race, religion, and insurance coverage.

* * * * *